United States Patent [19]

Ohashi et al.

[11] Patent Number: 4,562,263

[45] Date of Patent: Dec. 31, 1985

[54] PROCESS FOR PRODUCING 3-(3,4-DIHYDROXYPHENYL) SERINE

[75] Inventors: Naohito Ohashi, Brighton, Mass.; Shoji Nagata; Kikuo Ishizumi, both of Toyonaka, Japan

[73] Assignee: Sumitomo Chemical Company, Limited, Osaka, Japan

[21] Appl. No.: 614,246

[22] Filed: May 25, 1984

[30] Foreign Application Priority Data

May 25, 1983 [JP] Japan .................................. 58-92941
Feb. 15, 1984 [JP] Japan .................................. 59-27827
Feb. 15, 1984 [JP] Japan .................................. 59-27828

[51] Int. Cl.[4] ..................... C07D 209/48; C07C 99/12
[52] U.S. Cl. ..................................... 548/479; 562/444
[58] Field of Search ................... 564/444, 445, 446; 548/479

[56] References Cited

U.S. PATENT DOCUMENTS

| | | | |
|---|---|---|---|
| 3,723,514 | 3/1973 | Hegedus et al. | 260/519 |
| 4,242,256 | 12/1980 | Sharpe et al. | 548/479 |
| 4,275,217 | 6/1981 | Duhamal et al. | 548/479 |
| 4,319,040 | 3/1982 | Ohashi et al. | 562/444 |

FOREIGN PATENT DOCUMENTS

| | | | |
|---|---|---|---|
| 205027 | 8/1959 | Austria | 548/479 |
| 0024210 | 2/1981 | European Pat. Off. | 562/444 |
| 0084928 | 8/1983 | European Pat. Off. | 562/444 |
| 2034529 | 11/1970 | France | 562/444 |
| 2241302 | 8/1974 | France | 562/444 |
| 140036 | 2/1980 | German Democratic Rep. | 548/479 |
| 2000779 | 7/1977 | United Kingdom | 562/444 |

OTHER PUBLICATIONS

Hoffmann et al., J. Org. Chem., vol. 27, pp. 4686–4688 (1962).

Fieser et al., "Reagents For Organic Synthesis", pp. 111–112, 882 (1967).

*Primary Examiner*—James H. Reamer
*Attorney, Agent, or Firm*—Stevens, Davis, Miller & Mosher

[57] ABSTRACT

A process for producing racemic or optically active threo- or erythro-3-(3,4-dihydroxyphenyl)serine which comprises phthaloylating the amine group of a racemic or optically active threo- or erythro-3-(3,4-dihydroxyphenyl)serine derivative to yield a racemic or optically active threo- or erythro-N-phthaloyl-3-(3,4-dihydroxyphenyl)serine derivative and removing the phthaloyl group from the racemic or optically active threo- or erythro-N-phthaloyl-3-(3,4-dihydroxyphenyl)-serine to yield the racemic or optically active threo- or erythro-3-(3,4-dihydroxyphenyl)serine.

7 Claims, No Drawings

PROCESS FOR PRODUCING 3-(3,4-DIHYDROXYPHENYL) SERINE

This invention relates to a process for producing racemic or optically active threo- or erythro-3-(3,4-dihydroxyphenyl)serine represented by the formula

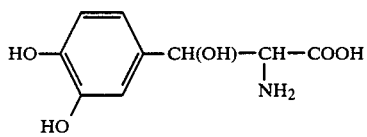
[I]

More particularly, it relates to a process for producing racemic or optically active threo- or erythro-3-(3,4-dihydroxyphenyl)serine represented by the above formula [I], which comprises phthaloylating the amino group of a racemic or optically active threo- or erythro-3-(3,4-dihydroxyphenyl)serine derivative repesented by the general formula

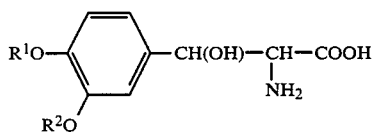
[IV]

(wherein $R^1$, and $R^2$ each represents a hydrogen atom or a methyl group, or $R^1$ and $R^2$ jointly form a methylene group, provided that $R^1$ and $R^2$ do not simultaneously represent hydrogen atoms) to yield a racemic or optically active threo- or erythro-N-phthaloyl-3-(3,4-dihydroxyphenyl)serine derivative represented by the general formula

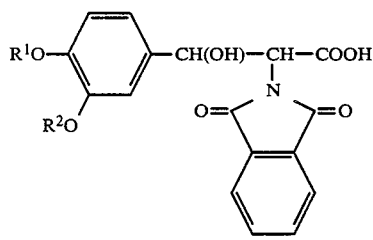
[III]

wherein $R^1$ and $R^2$ are as defined above; if necessary in the case in which the compound of formula [III] is in racemic form, subjecting the racemate to optical resolution through the reaction with one of the optically active amines to yield an optically active threo- or erythro N-phthaloyl-3-(3,4-dihydroxyphenyl)serine derivative represented by the general formula [III]; treating the racemic or optically active threo- or erythro-N-phthaloyl-3-(3,4-dihydroxyphenyl)serine derivative represented by the above formula [III] with a Lewis acid to yield racemic or optically active threo- or erythro-N-phthaloyl-3-(3,4-dihydroxyphenyl)serine represented by the formula

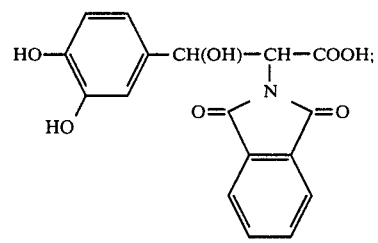
[II]

if necessary in the case in which the compound of formula [II] is in racemic form, subjecting the racemate to optical resolution through the reaction with one of the optically active amines to yield an optically active threo- or erythro-N-phthaloyl-3-(3,4-dihydroxyphenyl)serine represented by the above formula [II]; and removing the phthaloyl group from the racemic or optically active threo- or erythro-N- phthaloyl-3-(3,4-dihydroxyphenyl)serine represented by the above formula [II] to yieldthe racemic or optically active threo- or erythro-3-(3,4-dihydroxyphenyl)serine represented by the above formula [I].

The racemic or optically active threo-DOPS [DOPS stands for 3-(3,4-dihydroxyphenyl)serine] [I], which is obtained by the present process, is known to be pharmaceutically useful as a remedy for peripheral orthostatic hypotension [Japanese Patent Application "Kokai" (Laid-open) No. 104,815/81], as an antidepressant [Japanese Patent Application "Kokai" (Laid-open) No. 80,747/80], or as a remedy for parkinsonism [Japanese Patent Application "Kokai" (Laid-open) No. 52,219/83]. The racemic or optically active erythro-DOPS, on the other hand, is a useful compound known to have an anti-hypertensive activity [Japanese Patent Application "Kokai" (Laid-open) No. 49,252/75].

There is known a process for producing racemic or optically active threo- or erythro-DOPS, in which a protocatechualdhyde of the formula

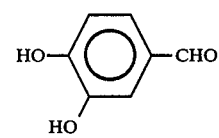

is used as a starting material. This aldehyde may be obtained from vanilline, veratraldehyde or piperonal wherein its catechol moiety is protected each by a methyl group, two methyl groups or a methylene group. Thus, the procedure of these methods comprises removing the methyl or methylene groups from vanilline, veratraldehyde or piperonal to yield protocatechualdehyde, protecting again the catechol moiety with ethoxycarbonyl or benzyl groups to form a benzaldehyde derivative of the formula

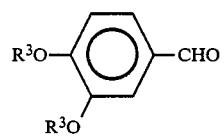
[V]

(wherein $R^3$ represents ethoxycarbonyl or benzyl group), condensing the resulting benzaldehyde derivative with glycine or a derivative thereof to obtain a mixture of threo- and erythro-DOPS derivatives, subjecting, if necessary, the resulting mixture to optical resolution, and removing the protective groups to yield racemic or optically active DOPS [Chem. Ber., 52, 1724 (1919); J. Chem. Soc., 658 (1947); Chem. Ber., 87, 892 (1954); J. Am. Chem. Soc., 76, 1322 (1954); Helv. Chim. Acta., 58, 157 (1975)]. Thus, in preparing DOPS the conventional process has a disadvantage in that it requires a complicated procedure of changing the protective group in catechol moiety of the benzaldehyde derivative used as starting material.

Under the circumstances, the present inventors carried out an extensive study to find a process for producing racemic or optically active DOPS, which requires no change of protective group. As a result, they found the present process in which the methyl or methylene group retained by the compound such as vanillin, veratraldehyde, or piperonal is used as the protective group for catechol, and accomplished the present invention.

The present invention is predicated upon the following discoveries:

(1) A racemic or optically active threo- or erythro-N-phthaloyl-DOPS derivative represented by the general formula [III] is obtained in high yield by the reaction of a phthaloylating agent with a racemic or optically active threo- or erythro-DOPS derivative represented by the general formula [IV] which is obtained directly from an aldehyde derivative such as vanillin, veratraldehyde, or piperonal without removing the methyl or methylene group.

(2) By the treatment with a Lewis acid of a racemic or optically active threo- or erythro-N-phthaloyl-DOPS derivative [III], it is possible to remove only the methyl or methylene group in the catechol moiety in spite of the presence of carboxyl, hydroxyl, and imido groups in the same molecule.

(3) By treating racemic or optically active threo- or erythro-N-phthaloyl-DOPS [II] with hydrazine, it is possible to obtain the corresponding racemic or optically active threo- or erythro-DOPS in high yield.

(4) The racemic threo- or erythro-N-phthaloyl-DOPS derivative [III] and racemic threo- or erythro-N-phthaloyl-DOPS [II] can be optically resolved by using as optically resoluting agent an optically active amine which is suitable for industrial use to yield the corresponding compound in optically active form (D- or L-form).

Thus, the present invention provides a commercially practicable and economical process for producing a racemic or optically active DOPS. The invention is described below in further detail.

A novel racemic or optically active threo- or erythro-N-phthaloyl-DOPS derivative [III] is obtained by treating a racemic or optically active threo- or erythro-DOPS derivative [IV] with a phthaloylating agent such as phthalic anhydride or N-ethoxycarbonylphthalimide. An optically active threo- or erythro-N-phthaloyl-DOPS derivative [III] is obtained by reacting said racemic N-phthaloyl derivative with one of the optically active amines selected from strychnine, cinchonidine, ephedrine, norephedrine, dehydroabietylamine, R-2-amino-1,1-diphenyl-1propanol, S-2-amino-1,1-diphenyl-1-propanol, and L-3-hydroxy-3-(4-nitrophenyl)-2-amino-1-propanol to from a mixture of amine salts of D- and L-threo- or erythro-N-phthaloyl-DOPS derivative, separating the mixture by taking advantage of the solubility difference into the amine salt of L-threo- or erythro-N-phthaloyl-DOPS derivative and the amine salt of D-threo- or erythro-N-phthaloyl-DOPS derivative, and finally reacting each amine salt with an acid.

It has heretofore been unknown to obtain a corresponding N-phthaloyl-DOPS [II] from a racemic or optically active threo- or erythro-N-phthaloyl-DOPS derivative [III]. In general, various methods are known for the regeneration of catechol group by removing a methyl or methylene group from a compound having these groups in the catechol moiety. However, as for the compound having amino and carboxyl group in the molecule in addition to the methyl or methylene group in the catechol moiety, an example is reported, in which 3-(3,4-methylenedioxyphenyl)alanine or an N-acetyl derivative thereof is treated with hydroiodic acid and acetic anhydride in the presence of red phosphorus to yield 3-(3,4-dihydroxyphenyl)alanine [Chem. Pharm. Bull., 10, 693 (1962)]; in another example, 2-methyl-3-(3,4-dimethoxyphenyl)alanine is treated with 47.5% hydrobromic acid under reflux to yield 2-methyl-3-(3,4-dihydroxyphenyl)alanine [J. Amer. Chem. Soc., 77, 700 (1955)]. These reaction conditions were found unadaptable to the removal of methyl or methylene group from the catechol moiety in the process of the present invention.

The present inventors conducted an extensive study on the conversion of a racemic or optically active threo- or erythro-N-phthaloyl-DOPS derivative [III] having hydroxy, imido, and carboxyl groups in addition to the methyl or methylene group in the catechol moiety into corresponding N-phthaloyl-DOPS [II] and, as a result, found that such conversion can be achieved by treating the former with a Lewis acid under mild conditions. It is desirable to add a mercaptan in addition to a Lewis acid to the reaction system.

Racemic threo- or erythro-N-phthaloyl-DOPS [II] is convertible into corresponding optically active (D and L) threo- or erythro-N-phthaloyl-DOPS by optical resolution technique with an optically active amine. For this purpose, it is thus possible to obtain an optically active threo- or erythro-N-phthaloyl-DOPS by reacting said racemic N-phthaloyl-DOPS with one of the optically active amines selected from quinidine, quinine, cinchonidine, cinchonine, ephedrine, norephedrine, l-menthylamine, and S-2-amino-1,1-diphenyl-1-propanol to form a mixture of amine salts of corresponding D- and L-threo(or erythro)-N-phthaloyl-DOPS, separating the mixture by taking advantage of solubility difference into tha amine salt of D-threo- or erythro-N-phthaloyl-DOPS and the amine salt of L-threo- or erythro-N-phthaloyl-DOPS, and finally reacting each amine salt with an acid.

The preparation of corresponding DOPS [I] from racemic or optically active threo- or erythro-N-phthaloyl-DOPS [II] is performed by customary dephthaloylation with hydrazine or the like.

The above procedure may be summarized in the following reaction scheme:

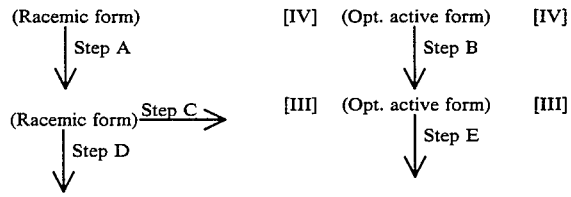

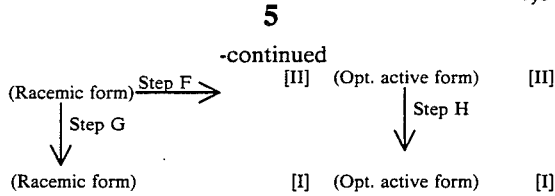

Each steps are described below.

(1) Steps A and B

The steps A and B are identical in chemical reaction, though different in starting compound which is a racemate, optical isomer, or erythro-threo configuration isomer. By the reaction of a racemic or optically active threo- or erythro-DOPS derivative [IV] with a phthaloylating agent such as phthalic anhydride N-carbethoxyphthalimide, or the like, there is obtained the corresponding N-phthaloyl-DOPS derivative [III]. The reaction is carried out under those conditions which are generally use, including molar ratio, solvent, reaction temperature, and reaction time.

(2) Step C

In this step, a racemic threo- or erythro-N-phthaloyl-DOPS derivative [III] is subjected to optical resolution to yield an optically active (D or L)-threo- or erythro-N-phthaloyl-DOPS derivative [III].

The racemic threo- or erythro-N-phthaloyl-DOPS derivative [III] is allowed to react in a suitable solvent with one of the optically active amines selected from strychnine, cinchonidine, ephedrine, norephedrine, dehydroabietylamine, R-2-amino-1,1-diphenyl-1-propanol S-2-amino-1,1-diphenyl-1-propanol, and L-3hydroxy-3-(4-nitrophenyl)-2-amino-1-propanol to yield a mixture of the salts of corresponding D- and L-threo- or erythro-N-phthaloyl-DOPS derivative with the optically active amine, then the mixture is separated by taking advantage of solubility difference into the optically active amine salt of D-threo- or erythro-N-phthaloyl-DOPS derivative and the optically active amine salt of L-threo- or erythro-N- phthaloyl-DOPS derivative, and each salt is decomposed with an acid. The formation and separation of the amine salt are performed either at a temperature of from 0° to 80° C. or by heating to a temperature near the boiling point of the solvent and cooling to 0° to 30° C. The salt formation sufficiently proceeds in several minutes, but the reaction time may be extended to several hours without causing any disturbance. The optically active amine is used in an amount of 0.5 to 1 mole for 1 mole of the racemic threo- or erythro-N-phthaloyl-DOPS derivative [III]. Examples of suitable solvents used in the formation and separation of salt are alcoholic solvents such as methanol, ethanol, and isopropyl alcohol, ether-type solvents such as tetrahydrofuran and dioxane; acetonitrile, water, and mixtures thereof.

The optically active threo- or erythro-N-phthaloyl-DOPS derivative [III] is obtained by decomposing, with an aqueous acid solution, the salt of optically active threo (or erythro)-N-phthaloyl-DOPS derivative [III] with the optically active amine which is obtained above, and extracting with an organic solvent. The suitable acids in the aqueous acid solution are mineral acids such as hydrochloric acid, sulfuric acid, and phosphoric acid. The acid is used in an amount of 1 mole or more, e.g. 1 to 10 moles, for 1 mole of the salt. Examples of suitable solvents for the extraction are ethyl acetate, chloroform, dichloroethane, dichloromethane, and diethyl ether.

(3) Steps D and E

The steps D and E are identical in chemical reaction, though different in starting material which is a racemate, optically active isomer or erythro-threo configuration isomer. When a racemic or optically active threo- or erythro-N-phthaloyl-DOPS derivative [III] is treated with a Lewis acid in a suitable solvent, a corresponding racemic or optically active threo- or erythro-N-phthaloyl-DOPS [II] is obtained. Examples of preferred Lewis acids are aluminum chloride, aluminum bromide, ferric chloride, stannic chloride, boron trichloride, and boron tribromide. A complex of Lewis acid with dimethyl sulfide may be used as a Lewis acid. The Lewis acid is used in an amount of 1 to 20, preferably 2 to 10, moles per 1 mole of threo- or erythro-DOPS derivative [III]. To obtain a more desirable result, there may be added, in addition to a Lewis acid, to the reactant mixture 1 to 5 moles of a mercaptan having 1 to 20 carbon atoms such as methyl mercaptan, ethyl mercaptan, butyl mercaptan, octyl mercaptan, dodecyl mercaptan, and octadecyl mercaptan per 1 mole of the Lewis acid. As the reaction solvent, there may be used any solvent unless it interferes with the progress of reaction. Preferred solvents include halogenated hydrocarbon solvents such as dichloromethane, chloroform, dichloroethane, and chlorobenzene; aromatic hydrocarbon solvents such as toluene and benzene; ester-type solvents such as ethyl acetate and butyl acetate; nitro hydrocarbons such as nitromethane, nitroethane, and nitrobenzene; ketone-type solvents such as acetone and methyl ethyl ketone; pyridine and mixtures thereof. The reaction temperature is in the range of from −40° to 80° C., preferably from −10° to 30° C. The reaction is complete in a period of from 10 minutes to 4 hours, though a prolonged reaction time causes no disturbance.

(4) Step F

In order to obtain an optically active threo- or erythro- N-phthaloyl-DOPS [II] from racemic threo- or erythro-N-phthaloyl-DOPS [II], the latter is allowed to react with one of the optically active amines selected from quinidine, quinine, cinchonidine, cinchonine, ephedrine, norephedrine, l-menthylamine, and S-2-amino-1,1-diphenyl-1-propanol to yield a mixture of amine salts of corresponding D- and L-threo- or erythro-N-phthaloyl-DOPS, then the mixture is separated, by taking advantage of solubility difference, into the optically active amine salt of D-threo- or erythro-N-phthaloyl-DOPS and the optically active amine salt of L-threo- or erythro-N-phthaloyl-DOPS, and each salt is allowed to react with an acid to produce optically active threo- or erythro-N-phthaloyl-DOPS [II]. The above optical resolution is performed under the same conditions (molar ratio, solvent, temperature, time, and conditions for the salt decomposition) as those employed in the optical resolution of racemic threo- or erythro-N-phthaloyl-DOPS derivative [III], except for the difference in the type of optically active amine used as the optical resolution agent.

(5) Steps G and H

The steps G and H are identical in chemical reaction, though different in starting material which is a racemate, optically active isomer or erythro-threo configuration isomer. By the reaction of racemic or optically active threo- or erythro-N-phthaloyl-DOPS with hydrazine, there is formed corresponding racemic or optically active DOPS. Hydrazine, which may be anhydrous or hydrated, is used in an amount of 1 to 20, preferably 2 to 5, moles for 1 mole of threo- or erythro-N-phthaloyl-DOPS [II]. As the solvent, there may be used water, alcohol-type solvents such as methanol, ethanol and isopropyl alcohol; ether-type solvents such as dioxane and tetrahydrofuran; halogenated hydrocarbon type solvents such as chloroform and 1,2-dichloroethane; and mixtures thereof. The reaction proceeds at room temperature and can be accelerated by the elevation of temperature up to the boiling point of the solvent.

The compounds represented by the formulas [II] and [III] involved in the present process are novel compounds which were first synthesized by the present inventors and were found to be useful as the intermediates for the synthesis of DOPS. Among the compounds represented by the general formula [IV], the racemic and optically active compounds in which $R^1$ is a hydrogen atom and $R^2$ is a methyl group are known (U.S. Pat. No. 3,723,514) and the racemic compound in which $R^1$ and $R^2$ jointly forms a methylene group is also known [Japanese Patent Application "Kokai" (Laid-open) Nos. 121,258/83 and 216,146/83]. Although the compounds of formula [IV] in which both $R^1$ and $R^2$ are methyl groups are already known [Can. J. Chem., 42, 1901 (1964); Texas Repts., Biol. and Med., 13, 195 (1955)], yet the steric threo-erythro configuration isomers have never been known and first isolated as such by the present inventors.

The racemic threo-form of the compound represented by the general formula [IV] in which both $R^1$ and $R^2$ are methyl groups is obtained by allowing glycine and veratraldehyde to react in the presence of an inorganic base such as potassium hydroxide in an organic solvent such as methanol, then adding water and acetic acid to the reaction mixture to decompose the intermediate reaction product, washing the mixture with an organic solvent such as toluene, allowing the mixture to stand, and recrystallizing the precipitated racemic threo-3-(3,4-dimethoxyphenyl)serine acetate from water. The optically active form is obtained by allowing the said acetate to react with carbobenzoxy chloride to form racemic threo-N-carbobenzoxy-3-(3,4-dimethoxyphenyl)serine, subjecting the resulting racemic mixture to optical resolution and subsequent catalytic reduction. On the other hand, the said racemic erythro-form is obtained by allowing to stand the mother liquor recovered from the recrystallization of the said racemic threo-form, and recrystallizing the precipitated crystals containing a high proportion of erythro-form from a water-acetic acid system. The optically active form is obtained similarly to the case of racemic threo-form.

The invention is illustrated below in detail with reference to Examples and Reference Examples, but the invention is not limited thereto.

REFERENCE EXAMPLE 1

Into 1,040 ml of methanol containing 55 g of potassium hydroxide dissolved therein, was dissolved 29.7 g of glycine. After addition of 144.5 g of veratraldehyde, the mixture was stirred for 30 minutes at 62° to 65° C., and then the mixture was concentrated. The residue was dissolved in 285 ml of methanol, mixed with 725 g of acetic acid, and stirred for 30 minutes at 40° to 45° C. After addition of 120 g of water and 900 g of toluene, the mixture was stirred for 2 hours at 40° to 45° C. The mixture was allowed to separate into two layers. The aqueous layer containing acetic acid was washed with a mixture of 300 ml of toluene and 300 ml of diethyl ether, and left standing for 15 hours. The precipitated crystals were collected by filtration to yield 21.72 g of racemic theo/erythro-3-(3,4-dimethoxyphenyl)serine (threo/erythro=7/3) melting at 182° C. (decomp.). A 20 g portion of the crystals was recrystallized from 100 ml of water to obtain 6.0 g of racemic threo 3-(3,4-dimethoxyphenyl)serine melting at 190° C. (decomp.).

IR: $\nu$ liquid paraffin (cm$^{-1}$) 3360, 3150, 1660, 1600, 1510, 1340, 1240, 1150, 1020, NMR: $\delta_{DMSO-d_6}{}^{TMS}$ (ppm), 3.39 (d,1H), 3.75 (s,3H), 3.77 (s,3H), 5.05 (d,1H), 6.7–7.1 (m,3H).

REFERENCE EXAMPLE 2

217.2 g of racemic threo/erythro-3-(3,4-dimethoxyphenyl)serine (threo/erythro=4/6) was recrystallized from a mixture of 54.3 g of acetic acid and 1,630 ml of water to yield 18.2 g of racemic erythro-3-(3,4-dimethoxyphenyl)serine melting at 183°–5° C.

IR: $\nu$ Liquid paraffin (cm$^{-1}$) 3200, 1600, 1515, 1410, 1315, 1255, 1230, 1130, 1020, NMR: $\delta_{CF_3COOD}{}^{TMS}$ (ppm) 3.93 (s,6H), 4.78 (d,1H,J=5 Hz), 5.17 (d,1H,J=5 Hz), 7.07 (s,3H).

REFERENCE EXAMPLE 3

Into 800 ml of an aqueous solution containing 20 g of sodium hydroxide, while being cooled at 5° C. or below, was added 59.0 g of racemic threo-3-(3,4-methylenedioxyphenyl)serine. After dissolution, to the solution maintained at 5° C. or below, was added dropwise 47.0 g of carbobenzoxy chloride, while pH of the reaction system being adjusted to 8.5–9.5 by simultaneously adding dropwise a 30% aqueous sodium hydroxide solution. Two hours after completion of the dropwise addition, the reaction mixture was adjusted to approximately pH 2 with concentrated hydrochloric acid and extracted with ethyl acetate. The organic layer was washed with a saturated aqueous sodium chloride solution, dried over anhydrous magnesium sulfate, and evaporated under reduced pressure. The residue was crystallized with toluene and the crystals were collected by filtration to obtain 89.0 g of racemic threo-N-carbobenzoxy-3-(3,4-methylenedioxyphenyl)serine melting at 136°–138° C.

To a solution of 50.0 g of the above compound in 500 ml of acetonitrile, was added 45.1 g of quinidine to form a clear solution. The mixture was cooled in icewater for 5 hours, and the precipitated crystals were collected by filtration to obtain 45.0 g of the quinidine salt of L-threo-N-carbobenzoxy-3-(3,4-methylenedioxyphenyl)serine melting at 161°–163° C.; $[\alpha]_D^{20} = +119.5°$ (C=1.0, methanol).

A portion (36.0 g) of the salt was recrystallized twice from methanol to obtain 26.4 g of the salt melting at 162°–163.5° C.; $[\alpha]_D^{20} = +122.6°$ (C=1.0, methanol).

To 24.0 g of the salt, was added 3% hydrochloric acid. The mixture was extracted with ethyl acetate, the extracts were dried and evaporated to obtain 10.8 g of an amorphous powder of L-threo-N-carbobenzoxy-3-(3,4-methylenedioxyphenyl)serine; $[\alpha]_D^{20} = -28.1°$ (C=1.0, methanol).

Into 880 ml of methanol, was dissolved 10.16 g of the above L-threo-N-carbobenzoxy-3-(3,4-methylenedioxyphenyl)serine. To the solution, were added 1.04 g of 10% Pd-C (containing 50% of water) and 10.16 g of water. The mixture was subjected to catalytic reduction under hydrogen at atmospheric pressure. After the hydrogen absorption had no longer been observed, 4.0 g of concentrated hydrochloric acid was added to the reaction mixture and the mixture was stirred. The insolubles were removed by filtration and the mother liquor was adjusted to approximately pH 5.5 with a 30% aqueous sodium hydroxide solution. The precipitated crystals were collected by filtration and recrystallized from water to obtain 4.16 g of L-threo-3-(3,4-methylenedioxyphenyl)serine melting at 196°–198° C. (decomp.); $[\alpha]_D^{25} = -31.3°$ (C=1.0, 1N HCl).

REFERENCE EXAMPLE 4

Synthesis of standard samples of racemic and L-threo-N-phthaloyl-3-(3,4-dihydroxyphenyl)serine:

(1) Into 200 ml of water, were dissolved 20 g of racemic threo-3-(3,4-dihydroxyphenyl)serine and 11.94 g of anhydrous sodium carbonate. To the resulting solution, while being maintained at 5° C. or below, was added 28.8 g of N-carbethoxyphthalimide. The mixture was stirred at room temperature for 15 hours and removed of insolubles by filtration. The filtrate was slightly acidified with concentrated hydrochloric acid and extracted three times with 1,000 ml of ethyl acetate. The extracts were dried over anhydrous sodium sulfate, and removed of the ethyl acetate by evaporation. The residue was crystallized with diethyl ether and the crystals were collected by filtration to yield 20.9 g of racemic threo-N-phthaloyl-3-(3,4-dihydroxyphenyl)serine melting at 131° C. (decomp.).

(2) Into 100 ml of water, were dissolved 10 g of L-threo-3-(3,4-dihydroxyphenyl)serine and 5.97 g of anhydrous sodium carbonate. To the resulting solution, while being maintained at 5° C. or below, was added 14.4 g of N-carbethoxyphthalimide. The mixture was stirred at room temperature for 3 hours, then diluted with 100 ml of water, slightly acidified with concentrated hydrochloric acid, and extracted three times with 500 ml of ethyl acetate. The extracts were dried over anhydrous sodium sulfate, and evaporated under reduced pressure to obtain 10.5 g of a residue. The residue was crystallized with diethyl ether to yield 6.0 of L-threo-N-phthaloyl-3-(3,4-dihydroxyphenyl)serine melting at 187° C. (decomp.); $[\alpha]_D^{20} = -99.9°$ (C=1, methanol).

EXAMPLE 1

(1) Into 200 ml of water, were dissolved 20 g of racemic threo-3-(3,4-methylenedioxyphenyl)serine and 11.31 g of anhydrous sodium carbonate. To the resulting solution, while being maintained at 5° C. or below, was added 27.28 g of N-carbethoxyphthalimide. The mixture was then stirred at room temperature for 3 hours and slightly acidified with concentrated hydrochloric acid. The precipitated crystals were collected by filtration to yield 30.63 g of racemic threo-N-phthaloyl-3-(3,4-methylenedioxyphenyl)serine melting at 124° C.

(2) To a solution of 30 g of racemic threo-N-phthaloyl-3-(3,4-methylenedioxyphenyl)serine obtained above in (1) and 45 ml of ethyl mercaptan in 900 ml of dried dichloromethane, while being cooled at −10° to 0° C. with stirring, was added 67.5 g of anhydrous aluminum chloride. The mixture was stirred at −10° to 0° C. for 4 hours and added dropwise into 600 ml of a 5% aqueous oxalic acid solution maintained at 20° C. or below. The mixture was then heated at 30° to 40° C. and stirred for 30 minutes. Thereafter, the mixture was cooled to room temperature and stirred for 30 minutes. The precipitated crystals were collected by filtration to yield 22.0 g of racemic threo-N-phthaloyl-3-(3,4-dihydroxyphenyl)-serine melting at 130°–132° C.

(3) Into 200 ml of ethanol, was dissolved 20.6 g of racemic threo-N-phthaloyl-3-(3,4-dihydroxyphenyl)serine obtained above in (2). To the resulting solution, was added 4.5 g of hydrazine hydrate. The mixture was heated under reflux for 2 hours. The reaction mixture was concentrated under reduced pressure. The residue was admixed with 200 ml of methanol, adjusted to approximately pH 1 with concentrated hydrochloric acid, and stirred for 30 minutes. After removal of insolubles by filtration, the filtrate was adjusted to pH 5.5–6 with a 30% aqueous sodium hydroxide solution and the precipitated crystals were collected by filtration to yield 10.5 g of racemic threo-3-(3,4-dihydroxyphenyl)-serine melting at 222°–224° C.

EXAMPLE 2

(1) Into 200 ml of water, were dissolved 20 g of racemic erythro-3-(3,4-methylenedioxyphenyl)serine and 11.31 g of anhydrous sodium carbonate. To the resulting solution, while being maintained at 5° C. or below, was added 27.28 g of N-carbethoxyphthalimide. The mixture was stirred for 3 hours at room temperature, made slightly acidic with concentrated hydrochloric acid, and extracted with ethyl acetate. The extracts were washed with saturated aqueous sodium chloride solution, dried over anhydrous magnesium sulfate, and evaporated under reduced pressure. The residue was crystallized with 80 ml of methanol, and the crystals were collected by filtration to yield 29.63 g of racemic erythro-N-phthaloyl-3-(3,4-methylenedioxyphenyl)serine melting at 117°–120° C.

| Elementary analysis: | C % | H % | N % |
| --- | --- | --- | --- |
| Calculated for $C_{18}H_{13}O_7N \cdot CH_3OH$ | 58.94 | 4.49 | 3.62 |
| Found | 58.76 | 4.41 | 3.60 |

(2) To a solution of 24.5 g of racemic erythro-N-phthaloyl-3-(3,4-methylenedioxyphenyl)serine obtained above in (1) and 71.3 g of n-octyl mercaptan in 740 ml of dried dichloromethane, while being cooled at −10° to 0° C. with stirring, was added 65.0 g of anhydrous aluminum chloride. The mixture was stirred at −10° to 0° C. for 4 hours and added dropwise into 430 ml of a 5-% aqueous oxalic acid solution at 20° C. or below. The mixture was then heated to 30° to 40° C. for 30 minutes with stirring. The mixture was further stirred at room temperature for 30 minutes. The precipitated crystals were collected by filtration to yield 20.6 g of racemic erythro-N-phthaloyl-3-(3,4-dihydroxyphenyl)serine melting at 93°–95° C.

IR: ν liquid paraffin (cm$^{-1}$) 3400, 1700, 1610, 1510, 1400, 1380, 1190, 1110, 1010.

(3) Into 200 ml of ethanol, was dissolved 20.6 g of racemic erythro-N-phthaloyl-3-(3,4-dihydroxyphenyl)serine. To the resulting solution, was added 4.5 g of hydrazine hydrate. After having been heated under reflux for 2 hours, the reaction mixture was adjusted to approximately pH 1 with concentrated hydrochloric acid, stirred for 30 minutes, and removed the insolubles by filtration. The filtrate was adjusted to approximately pH 5.5–5.6 with a 30% aqueous sodium hydroxide solution, and evaporated under reduced pressure. The residue was dissolved in 140 ml of water with heating and left standing for 15 hours at 0° to 5° C. The precipitated crystals were collected by filtration to yield 8.33 g of racemic erythro-3-(3,4-dihydroxyphenyl)serine melting at 215°–218° C.

| Elementary analysis: | C % | H % | N % |
| --- | --- | --- | --- |
| Calculated for $C_9H_{11}O_5N \cdot H_2O$ | 46.75 | 5.67 | 6.06 |
| Found | 46.84 | 5.78 | 6.06 |

EXAMPLE 3

(1) Into 50 ml of water, were dissolved 5.0 g of racemic threo-3-(3,4-dimethoxyphenyl)serine obtained in Reference Example 1 and 2.3 g of anhydrous sodium carbonate. To the resulting solution, while being maintained at 5° C. or below with stirring, was added 5.13 g of N-carbethoxyphthalimide. The mixture was stirred at room temperature for 15 hours, diluted with 200 ml of water, and made slightly acidic with concentrated hydrochloric acid. The precipitated crystals were collected by filtration to yield 5.34 g of racemic threo-N-phthaloyl-3-(3,4-dimethoxyphenyl)serine melting at 97° C. (decomp.).

(2) Into a mixture of 0.5 g of racemic threo-N-phthaloyl-3-(3,4-dimethoxyphenyl)serine obtained above in (1), 0.75 ml of ethyl mercaptan, and 15 ml of dried dichloromethane, while being cooled at 5° C. or below with stirring, was added 1.44 g of anhydrous aluminum bromide. To the mixture which had been stirred for 2 hours at room temperature, were added 0.75 ml of ethyl mercaptan and 1.44 g of anhydrous aluminum bromide. The mixture was stirred for 72 hours at room temperature. The mixture was added dropwise into 50 ml of a 5% aqueous oxalic acid solution at 20° C. or below. The reaction mixture was extracted three times with 50 ml of ethyl acetate. The extracts were washed three times with 50 ml of saturated aqueous sodium chloride solution, dried over anhydrous sodium sulfate, and evaporated under reduced pressure. The residue was crystallized from diethyl ether to yield 0.3 g of racemic threo-N-phthaloyl-3-(3,4-dihydroxyphenyl)serine melting at 128°–132° C.

(3) To a solution of 0.21 g of racemic threo-N-phthaloyl-3-(3,4-dihydroxyphenyl)serine obtained above in (2) dissolved in 2 ml of ethanol, was added 0.045 g of hydrazine hydrate. The mixture was heated under reflux for 2 hours and the reaction mixture was concentrated under reduced pressure. The residue was admixed with 2 ml of methanol, adjusted to pH 1 with concentrated hydrochloric acid, then stirred for 30 minutes, and removed the insolubles by filtration. The filtrate was adjusted to pH 5.5–6 with a 30% aqueous sodium hydroxide solution, and the precipitated crystals were collected by filtration to yield 0.1 g of racemic threo-3-(3,4-dihydroxyphenyl)serine melting at 222°–225° C.

EXAMPLE 4

(1) Into 50 ml of water, were dissolved 5.0 g of racemic threo/erythro-3-(4-hydroxy-3-methoxyphenyl)-serine (threo/erythro $\approx$ 3/2) and 2.8 g of anhydrous sodium carbonate. To the resulting solution, while being maintained at 5° C. or below with stirring, was added 6.75 g of N-carbethoxyphthalimide. The mixture was stirred for 3 hours at room temperature, made slightly acidic with concentrated hydrochloric acid, and extracted three times with 500 ml of ethyl acetate. The extracts were dried over anhydrous sodium sulfate, and evaporated under reduced pressure to yield 12.1 g of racemic threo/erythro-N-phthaloyl-3-(4-hydroxy-3-methoxyphenyl)serine in oily form.

A portion of this oil was chromatographed with silica gel to obtain racemic threo-N-phthaloyl-3-(4-hydroxyl-3-methoxyphenyl)serine in oily form.

NMR: $\delta_{CDCl_3}^{TMS}$ (ppm): 3.6 (s,3H), 4.9 (d,1H), 5.22 (d,1H), 6.6–7.0 (m,3H), 7.92 (s,5H).

(2) Into a mixture of 1.0 g of racemic threo-N-phthaloyl-3-(4-hydroxy-3-methoxyphenyl)serine obtained above in (1), 3.5 ml of n-octyl mercaptan, and 150 ml of dried dichloromethane, while being cooled at 5° C. or below with stirring, was added 1.4 g of anhydrous aluminum chloride. To the mixture which had been stirred at room temperature for 15 hours, were added 2.1 g of anhydrous aluminum bromide and 3.5 ml of n-octyl mercaptan. To the mixture after 15 hours of stirring, were added again 2.1 g of anhydrous aluminum bromide and 3.5 ml of n-octyl mercaptan. The mixture was stirred for 40 hours, then added dropwise into 200 ml of a 5-% aqueous oxalic acid solution at 20° C. or below, and extracted with ethyl acetate. The extracts were dried over anhydrous sodium sulfate, and evaporated under reduced pressure. The residue was crystallized from diethyl ether to yield 0.14 g of racemic threo-N-phthaloyl-3-(3,4-dihydroxyphenyl)-serine melting at 122°–132° C.

(3) Into 1 ml of ethanol, was dissolved 0.11 g of racemic threo-N-phthaloyl-3-(3,4-dihydroxyphenyl)-serine obtained above in (2). To the resultiing solution, was added 0.023 g of hydrazine hydrate. The mixture was heated under reflux for 2 hours and the reaction mixture was concentrated under reduced pressure. The residue was mixed with 1 ml of methanol, adjusted to pH 1 with concentrated hydrochloric acid, stirred for 30 minutes, and removed insolubles by filtration. The filtrate was adjusted to pH 5.5–6 with a 30% aqueous sodium hydroxide solution and the precipitated crystals were collected by filtration to yield 0.05 g of racemic threo-3-(3,4-dihydroxyphenyl)serine melting at 222°–224° C.

EXAMPLE 5

(1) Into 50 ml of water, were dissolved 5.0 g of racemic erythro-3-(3,4-dimethoxyphenyl)serine obtained in Reference Example 2 and 2.3 g of anhydrous sodium carbonate. To the resulting solution, while being cooled to 5° C. or below with stirring, was added 5.13 g of N-carbethoxyphthalimide. The mixture was stirred for 3 hours at room temperature, diluted with 200 ml of water, then made slightly acidic with concentrated hydrochloric acid, and extracted with ethyl acetate. The extracts were washed with saturated aqueous sodium chloride solution, dried over anhydrous magnesium sulfate, and evaporated under reduced pressure to yield 5.34 g of racemic erythro-N-phthaloyl-3-(3,4-dimethoxyphenyl)serine in oily form.

NMR: $\delta_{CDCl_3}^{TMS}$ (ppm): 3.75 (s,6H), 5.05 (d,1H,J=9Hz), 5.52 (d,1H,J=9Hz), 6.67–6.83 (m,3H), 7.68 (m,4H).

(2) Into a mixture of 5.0 g of racemic erythro-N-phthaloyl-3-(3,4-dimethoxyphenyl)serine obtained above in (1), 14.3 g of n-octyl mercaptan, and 150 ml of dried dichloromethane, while being cooled to 5° C. or below with stirring, was added 14.4 g of anhydrous aluminum chloride. The mixture was stirred for 4 hours at 0° to 10° C., added dropwise into 100 ml of a 5% aqueous oxalic acid solution at 20° C. or below, then stirred at 30° to 40° C. for 30 minutes, and at room temperature for another 30 minutes. The precipitated crystals were collected by filtration to yield 4.40 g of racemic erythro-N-phthaloyl-3-(3,4-dihydroxyphenyl)serine melting at 93°–95° C.

(3) Into 20 ml of methanol, was dissolved 2.06 g of racemic erythro-N-phthaloyl-3-(3,4-dihydroxyphenyl)serine obtained above in (2). To the resulting solution, was added 0.45 g of hydrazine hydrate. The mixture was heated under reflux for 2 hours. The reaction mixture was adjusted to approximately pH 1 with concentrated hydrochloric acid, stirred for 30 minutes, and removed the insolubles by filtration. The filtrate was adjusted approximately to pH 5.5–5.6 with a 30% aqueous sodium hydroxide solution, and evaporated under reduced pressure. The residue was dissolved with heating in 13 ml of water and left standing for 15 hours at 0° to 5° C. The precipitated crystals were collected by filtration to yield 0.83 g of racemic erythro-3-(3,4-dihydroxyphenyl)serine melting at 215°–218° C.

EXAMPLE 6

(1) Into 50 ml of water, were dissolved 5.0 g of racemic threo/erythro-3-(4-hydroxy-3-methoxyphenyl)serine (threo/erythro $\approx$ 3/2) and 2.8 g of anhydrous sodium carbonate. To the resulting solution, while being maintained at 5° C. or below with stirring, was added 6.75 g of N-carbethoxyphthalimide. The mixture was stirred at room temperature for 3 hours, made slightly acidic with concentrated hydrochloric acid, and extracted three times with 500 ml of ethyl acetate. The extracts were dried over anhydrous sodium sulfate, and evaporated under reduced pressure to yield 12.1 g of racemic threo/erythro-N-phthaloyl-3-(4-hydroxy-3methoxyphenyl)serine in oily form. A portion of the oil was chromatographed with silica gel to yield racemic erythro-N-phthaloyl-3-(4-hydroxy-3-methoxyphenyl)serine in oily form.

NMR: $\delta_{CDCl_3}^{TMS}$ (ppm): 3.6 (s,3H), 4.7 (d,1H), 5.28 (d,1H), 6.4–6.8 (m,3H), 7.8 (s,5H).

(2) Into a mixture of 0.5 g of racemic erythro-N-phthaloyl-3-(4-hydroxy-3-methoxyphenyl)serine obtained above in (1), 1.43 g of n-octyl mercaptan, and 15 ml of dried dichloromethane, while being maintained at 5° C. or below with stirring, was added 1.44 g of anhydrous aluminum chloride. The mixture was stirred for 4 hours at 0° to 10° C., added dropwise into 10 ml of a 5% aqueous oxalic acid solution at 20° C. or below, then stirred at 30° to 40° C. for 30 minutes, and at room temperature for another 30 minutes. The precipitated crystals were collected by filtration to yield 0.44 g of racemic erythro-N-phthaloyl-3-(3,4-dihydroxyphenyl)serine melting at 93°–95° C.

(3) Into 4 ml of methanol, was dissolved 0.206 g of racemic erythro-N-phthaloyl-3-(3,4-dihydroxyphenyl)serine obtained above in (2). To the resulting solution, was added 0.045 g of hydrazine hydrate. The mixture was heated under reflux for 2 hours. The reaction mixture was adjusted approximately to pH 1 with concentrated hydrochloric acid, stirred for 30 minutes, and removed the insolubles by filtration. The filtrate was adjusted approximately to pH 5.5–5.6 with a 30% aqueous sodium hydroxide solution and evaporated under reduced pressure. The residue was dissolved with heating in 1.3 ml of water, and left standing for 15 hours at 0° to 5° C. The precipitated crystals were collected by filtration to yield 0.08 g of racemic erythro-3-(3,4-dihydroxyphenyl)serine melting at 215°–218 ° C.

EXAMPLE 7

Into 50 ml of water, were dissolved 4.0 g of L-threo-3-(3,4-methylenedioxyphenyl)serine obtained in Reference Example 3 and 2.25 g of anhydrous sodium carbonate. To the resulting solution, while being maintained at 5° C. or below with stirring, was added 5.45 g of N-carbethoxyphthalimide. The mixture was stirred for 3 hours at room temperature, then diluted with 50 ml of water, and made slightly acidic with concentrated hydrochloric acid. The precipitated crystals were collected by filtration to yield 5.95 g of L-threo-N-phthaloyl-3-(3,4-methylenedioxyhenyl)serine. A portion (2.5 g) of the crysals was recrystallized from ethyl acetate to yield 1.15 g of L-threo-N-phthaloyl-3-(3,4-methylenedioxyphenyl)serine melting at 119°–124° C.; $[\alpha]_D^{20} = -96.1°$ (C=1, methanol).

EXAMPLE 8

(1) Into 5 ml of methanol, were dissolved 0.5 g of racemic threo-N-phthaloyl-3-(3,4-methylenedioxyphenyl)-serine and 0.3 g of L-3-hydroxy-3-(4-nitrophenyl)-2-amino-1-propanol. The resulting solution was left standing for 5 hours at room temperature. The precipitated crystals were collected by filtration to yield 0.27 g of L-3-hydroxy-3-(4-nitrophenyl)-2-amino-1-propanol salt of L-threo-N-phthaloyl-3-(3,4-methylenedioxyphenyl)-serine; melting point, 189° C. (decomp.), $[\alpha]_D^{20}$, −17.8° (C=1, methanol). A portion of the salt was added to 10 ml of 1N hydrochloric acid and extracted twice with 20 ml of ethyl acetate. The extracts were washed with saturated aqueous sodium chloride solution, dried over anhydrous sodium sulfate, and evaporated under reduced pressure to yield L-threo-N-phthaloyl-3-(3,4-methylenedioxyphenyl)serine melting at 115°–120° C.; $[\alpha]_D^{20} = -38.7°$ (C=1, methanol).

(2) Into 2 ml of methanol, were dissolved 0.5 g of racemic threo-N-phthaloyl-3-(3,4-methylenedioxyphenyl)serine and 0.21 g of l-norephedrine. The resulting solution was left standing for 4 hours at room temperature. The precipitated crystals were collected by filtration to yield 0.24 g of l-norephedrine salt of L-threo-N-phthaloyl-3-(3,4-methylenedioxyphenyl)serine melting at 189° C. (decomp.); $[\alpha]_D^{20} = -84.7°$ (C=1, methanol). A portion of the salt was decomposed in the same manner as in (1) to yield L-threo-N-phthaloyl-3-(3,4-methylenedioxyphenyl)serine melting at 92°–100° C.; $[\alpha]_D^{20} = -94.5°$ (C=1, methanol).

(3) Into 10 ml of methanol, were dissolved 0.5 g of racemic threo-N-phthaloyl-3-(3,4-methylenedioxyphenyl)serine and 0.47 g of strychnine. The resulting solution was left standing for 3 hours at room temperature. The precipitated crystals were collected by filtration to yield 2.48 g of strychnine salt of L-threo-N-phthaloyl-3-(3,4-methylenedioxyphenyl)serine melting at 148°–152° C.; $[\alpha]_D^{20} = -88.6°$ (C=1, DMF). A portion of the salt was decomposed in the same manner as in (1) to yield L-threo-N-phthaloyl-3-(3,4-methylenedioxyphenyl)serine melting at 91°–97° C.; $[\alpha]_D^{20} = -72.6°$ (C=1, methanol).

(4) Into 150 ml of ethanol, were dissolved 15.0 g of racemic threo-N-phthaloyl-3-(3,4-methylenedioxyphenyl)-serine and 9.6 g of S-2-amino-1,1-diphenyl-1-propanol. The resulting solution was left standing for 15 hours at room temperature and the precipitated crysals were collected by filtration to yield 9.9 g of S-2-amino-1,1-diphenyl-1-propanol salt of L-threo-N-phthaloyl-3-(3,4-methylenedioxyphenyl)serine; melting point, 113°–125° C.; $[\alpha]_D^{20} = -24.1°$ (C=1.0, methanol). To 6.0 g of the salt, was added 26 ml of 1N hydrochloric acid. The mixture was stirred for 2 hours at room temperature. The precipitated crysals were collected by filtration to yield 4.18 g of L-threo-N-phthaloyl-3-(3,4-methylenedioxyphenyl)-serine melting at 90°–100° C.; $[\alpha]_D^{20} = -87.2°$ (C=1.0, methanol).

(5) Into 5 ml of dioxane, were dissolved 0.5 g of racemic threo-N-phthaloyl-3-(3,4-methylenedioxyphenyl)-serine and 0.41 g of cinchonidine. The resulting solution was left standing at room temperature for 48 hours and the precipitated crysals were collected by filtration to yield 0.12 g of cinchonidine salt of L-threo-N-phthaloyl-3-(3,4-methylenedioxyphenyl)serine melting at 202°–207° C.; $[\alpha]_D^{20} = -81.4°$ (C=1, methanol). A portion of the salt was decomposed in the same manner as in (1) above and there was obtained L-threo-N-phthaloyl-3-(3,4-methylenedioxyphenyl)serine melting at 118°–123° C.; $[\alpha]_D^{20} = -32.7°$ (C=1, methanol).

EXAMPLE 9

(1) Into 40 ml of methanol, was dissolved 0.25 g of racemic erythro-N-phthaloyl-3-(3,4-methylenedioxyphenyl)serine followed by 0.19 g of cinchonidine. The resulting solution was left standing for 48 hours at room temperature. The precipitated crysals were collected by filtration to yield 0.12 g of cinchonidine salt of L-erythro-N-phthaloyl-3-(3,4-methylenedioxyphenyl)serine melting at 230°–232° C.; $[\alpha]_D^{20} = -41.8°$ (C=1, DMSO), A portion of the salt was decomposed in the same manner as in (1) of Example 8 to yield L-erythro-N-phthaloyl-3-(3,4-methylenedioxyphenyl)serine in oily form; $[\alpha]_D^{20} = -4.5°$ (C=1, CHCl$_3$).

(2) Into 20 ml of ethanol, was dissolved 0.25 g of racemic erythro-N-phthaloyl-3-(3,4-methylenedioxyphenyl)serine followed by 0.216 g of strychnine. The resulting solution was left standing for 15 hours at room temperature. The precipitated crysals were collected by filtration to yield 0.08 g of strychnine salt of L-erythro-N-phthaloyl-3-(3,4-methylenedioxyphenyl)-serine melting at 144°–148° C.; $[\alpha]_D^{20} = -1.8°$ (C=1.0, CHCl$_3$). A portion of the salt was decomposed in the same manner as in (1) above to yield L-erythro-N-phthaloyl-3-(3,4-methylenedioxyphenyl)serine in oily form; $[\alpha]_D^{20} = -2.3°$ (C=1, CHCl$_3$).

(3) Into 200 ml of ethanol, was dissolved 22.0 g of racemic erythro-N-phthaloyl-3-(3,4-methylenedioxyphenyl)serine, followed by 12.9 g of S-2-amino-1,1-diphenyl-1-propanol. The resulting solution was left standing for 15 hours at room temperature and the precipitated crystals were collected by filtration to yield 12.51 g of S-2-amino-1,1-diphenyl-1-propanol salt of L-erythro-N-phthaloyl-3-(3,4-methylenedioxyphenyl)-serine; melting point, 118°–119° C.; $[\alpha]_D^{30} = -135.4°$ (C=1, chloroform). A portion (12.0 g) of the salt was recrystallized from 96 ml of ethanol to yield 10.98 g of the salt melting at 118°–119° C.; $[\alpha]_D^{30} = -137.6°$ (C=1, chloroform).

| Elementary analysis: | C % | H % | N % |
|---|---|---|---|
| Calculated for C$_{33}$H$_{30}$N$_2$O$_8$.C$_2$H$_5$OH | 66.87 | 5.77 | 4.46 |
| Found | 66.91 | 5.85 | 4.44 |

To 7.70 g of the above salt, were added 50 ml of 1N hydrochloric acid and 50 ml of ethyl acetate. The mixture was stirred for 30 minutes at room temperature and allowed to settle. The organic layer was washed with saturated aqueous sodium chloride solution, dried over anhydrous magnesium sulfate, and evaporated under reduced pressure to yield 4.35 g of L-erythro-N-phthaloyl-3-(3,4-methylenedioxyphenyl)serine in oily form; $[\alpha]_D^{25} = -172.5°$ (C=1, CHCl$_3$).

IR: $\nu$ liquid paraffin (cm$^{-1}$): 3500, 1700, 1600, 1240, 1160, 1090, 1020, 910.

EXAMPLE 10

(1) Into 5 ml of acetonitrile, were dissolved 0.5 g of racemic threo-N-phthaloyl-3-(3,4-methylenedioxyphenyl)serine and 0.4 g of dehydroabietylamine. The resulting solution was left standing for 72 hours at room temperature and the precipitated crystals were collected by filtration to yield 0.45 g of the dehydroabietylamine salt of D-threo-N-phthaloyl-3-(3,4-methylenedioxyphenyl)serine; melting point, 134°–138° C.; $[\alpha]_D^{20} = +14.6°$ (C=1, methanol). A portion of the salt was decomposed in the same manner as in Example 8-(1) to yield D-threo-N-phthaloyl-3-(3,4-methylenedioxyphenyl)-serine; melting point, 122°–124° C.; $[\alpha]_D^{20} = +5.1°$ (C=1, methanol).

(2) Into 5 ml of acetonitrile, were dissolved 0.5 g of racemic threo-N-phthaloyl-3-(3,4-methylenedioxyphenyl)serine and 0.23 g of ephedrine. The resulting solution was left standing for 15 hours at room temperature. The precipitated crystals were collected by filtration to yield 0.25 g of the ephedrine salt of D-threo-N-phthaloyl-3-(3,4-methylenedioxyphenyl)serine; melting point, 178°–182° C.; $[\alpha]_D^{20} = +42.0°$ (C=1.0, methanol). A portion of the salt was decomposed in the same manner as in Example 8-(1) to yield D-threo-N-phthaloyl-3-(3,4-methylenedioxyphenyl)serine; melting point, 120°–124° C.; $[\alpha]_D^{20} = +72.7°$ (C=1, methanol).

EXAMPLE 11

Into 200 ml of ethanol, was dissolved 22.0 g of racemic erythro-N-phthaloyl-3-(3,4-methylenedioxyphenyl)serine, followed by 12.9 g of R-2-amino-1,1-diphenyl-1-propanol. The resulting solution was left standing for 15 hours at room temperature. The precipitated crystals were collected by filtration to yield 12.51 g of the R-2-amino-1,1-diphenyl-1-propanol salt of D-erythro-N-phthaloyl-3-(3,4-methylenedioxyphenyl)-serine; melting point, 113°–116° C.; $[\alpha]_D^{30} = +135.4°$ (C=1, chloroform). A portion (12.0 g) of the above salt was recrystallized from 96 ml of ethanol to yield 10.98 g of the salt; melting point, 119°–121° C.; $[\alpha]_D^{30} = +141.6°$ (C=1, CHCl$_3$).

| Elementary analysis: | C % | H % | N % |
|---|---|---|---|
| Calculated for C$_{33}$H$_{30}$N$_2$O$_8$.C$_2$H$_5$OH | 66.87 | 5.77 | 4.46 |
| Found | 66.91 | 5.85 | 4.44 |

To 7.70 g of the above salt, were added 50 ml of 1N hydrochloric acid and 50 ml of ethyl acetate. The mixture was stirred for 30 minutes at room temperature and allowed to settle. The organic layer was washed with saturated aqueous sodium chloride solution, dried over anhydrous magnesium sulfate, and evaporated under reduced pressure to yield 4.35 g of D-erythro-N-phthaloyl-3-(3,4-methylenedioxyphenyl)serine in oily form; $[\alpha]_D^{25} = +172.5°$ (C=1, CHCl$_3$).

IR: ν liquid paraffin (cm$^{-1}$): 3500, 1700, 1600, 1240, 1160, 1090, 1020, 910.

EXAMPLE 12

(1) Into 10 ml of ethanol, was dissolved 0.245 g of racemic erythro-N-phthaloyl-3-(3,4-dihydroxyphenyl)serine obtained as in Example 2-(2), followed by the addition of 0.209 g of quinidine. The resulting solution was left standing for 15 hours at room temperature and the precipitated crystals were collected by filtration to yield 0.085 g of the quinidine salt of L-erythro-N-phthaloyl-3-(3,4-dihydroxyphenyl)serine; $[\alpha]_D^{25} = +69.0°$ (C=1, DMSO). A portion of the salt was decomposed as in Example 8-(1) to yield L-erythro-N-phthaloyl-3-(3,4-dihydroxyphenyl)serine in oily form; $[\alpha]_D^{26} = -3.0°$ (C=1, CHCl$_3$).

(2) Into 10 ml of ethanol, was dissolved 0.245 g of racemic erythro-N-phthaloyl-3-(3,4-dihydroxyphenyl)serine, followed by the additionof 0.190 g of cinchonidine. The resulting solution was left standing for 5 hours at room temperature. The precipitated crystals were collected by filtration to yield 0.088 g of the cinchonidine salt of L-erythro-N-phthaloyl-3-(3,4-dihydroxyphenyl)serine; melting point, 235°–240° C. (decomp.); $[\alpha]_D^{26} = +12.7°$ (C=1, DMSO). A portion of the salt was decomposed as in Example 8-(1) to yield L-erythro-N-phthaloyl-3-(3,4-dihydroxyphenyl)serine in oily form; $[\alpha]_D^{26} = -20.2°$ (C=1, CHCl$_3$).

(3) Into 5 ml of ethanol, was dissolved 0.245 g of racemic erythro-N-phthaloyl-3-(3,4-dihydroxyphenyl)serine, followed by the addition of 0.147 g of S-2-amino-1,1-diphenyl-1-propanol. The resulting solution was left standing for 5 hours at room temperature. The precipitated crystals were collected by filtration to yield 0.050 g of the S-2-amino-1,1-diphenyl-1-propanol salt of L-erythro-N-phthaloyl-3-(3,4-dihyroxyphenyl)-serine; melting point, 300° C. or above; $[\alpha]_D^{26} = +13.1°$ (C=1, DMSO). A portion of the salt was decomposed as in Example 8-(1) to yield L-erythro-N-phthaloyl-3-(3,4-dihydroxyphenyl)serine; $[\alpha]_D^{26} = -1.1°$ (C=1, CHCl$_3$).

(4) Into 10 ml of isopropyl alcohol, was dissolved 0.245 g of racemic erythro-N-phthaloyl-3-(3,4-dihydroxyphenyl)serine, followed by the addition of 0.098 g of norephedrine. The resulting solution was left standing for 15 hours at 0° to 5° C. The precipitated crystals were collected by filtration to yield 0.086 g of the norephedrine salt of D-erythro-N-phthaloyl-3-(3,4-dihydroxyphenyl)serine; melting point, 300° C. or above; $[\alpha]_D^{26} = +3.4°$ (C=1, CHCl$_3$). A portion of the salt was decomposed as in Example 8-(1) to yield D-erythro-N-phthaloyl-3-(3,4-dihydroxyphenyl)serine in oily form; $[\alpha]_D^{25} = +20.1°$ (C=1, CHCl$_3$).

EXAMPLE 13

(1) Into 5 ml of ethanol, were dissolved 0.5 g of racemic threo-N-phthaloyl-3-(3,4-dihydroxyphenol)-serine and 0.22 g of l-menthylamine. The resulting solution was left standing for 48 hours at 0° to 5° C. The precipitated crystals were collected by filtration to yield 0.44 g of the l-menthylamine salt of D-threo-N-phthaloyl-3-(3,4-dihydroxypenyl)serine; melting point, 191° C. (decomp.); $[\alpha]_D^{20} = -1.9°$ (C=1, methanol). A portion of the salt was decomposed as in Example 8-(1) to yield D-threo-N-phthaloyl-3-(3,4-dihydroxyphenyl)-serine; melting point, 171° C. (decomp.); $[\alpha]_D^{20} = +14.5°$ (C=1, methanol).

(2) Into 5 ml of dioxane, were dissolved 0.5 g of racemic threo-N-pthaloyl-3-(3,4-dihydroxyphenyl)-serine and 0.46 g of quinidine. The resulting solution was left standing for 20 days at room temperature. The precipitated crystals were collected by filtration to yield 0.55 g of the quinidine salt of D-threo-N-phthaloyl-3-(3,4-dihydroxyphenyl)serine; melting point, 134° (decomp.); $[\alpha]_D^{20} = -135.0°$ (C=1, methanol). A portion of the salt was decomposed as in Example 8-(1) to yield D-threo-N-phthaloyl-3-(3,4-dihydroxyphenyl)serine; melting point, 187° C. (decomp.); $[\alpha]_D^{20} = +74.3$ (C=1, methanol).

(3) Into 5 ml of methanol, were dissolved 0.5 g of racemic threo-N-phthaloyl-3-(3,4-dihydroxyphenyl)-serine and 0.46 g of quinidine. The resulting solution was left standing for 20 days at room temperature. The precipitated crystals were collected by filtration to yield 0.41 g of the quinine salt of D-threo-N-pthaloyl-3-(3,4-dihydroxyphenyl)serine; melting point, 180°–185° C.; $[\alpha]_D^{20} = -82.7°$ (C=1, methanol). A portion of the salt was decomposed in the same manner as in Example 8-(1) to yield D-threo-N-phthaloyl-3-(3,4-dihydroxyphenyl)serine; melting point, 175° C. (decomp.); $[\alpha]_D^{20} = +32.1°$ (C=1, methanol).

(4) Into 5 ml of methanol, were dissolved 0.5 g of racemic threo-N-pthaloyl-3-(3,4,-dihydroxyphenyl)-serine and 0.43 g of cinchonidin. The resulting solution was left standing for 5 hours at room temperature and the precipitated crystals were collected by filtration to yield 0.28 g of the cinchonidine salt of D-threo-N-phthaloyl-3-(3,4-dihydroxypenyl)serine; melting point, 165°–172° C.; $[\alpha]_D^{20} = -41.2°$ (C=1, methanol). A portion of the salt was decomposed as in Example 8-(1) to yield D-threo-N-phthaloyl-3-(3,4-dihyroxyphenyl)serine, melting point, 180° C. (decomp.); $[\alpha]_D^{20} = +44.7°$ (C=1, methanol).

(5) Into 5 ml of dioxane, were dissolved 0.5 g of racemic threo-N-phthaloyl-3-(3,4-dihydroxyphenyl)-serine and 0.43 g of cinchonine. The resulting solution was left standing for 5 hours at room temperature and the precipitated crystals were collected by filtration to yield 0.29 g of the cinchonine salt of D-threo-N-phthaloyl-3-(3,4-dihydroxyphenyl)serine; melting point, 154°–163° C.; $[\alpha]_D^{20} = +117.3°$ (C=1, methanol). A portion of the salt was decomposed as in Example 8-(1) to yield D-threo-N-phthaloyl-3-(3,4-dihydroxyphenyl)serine; melting point, 185° C. (decomp.); $[\alpha]_D^{20} = +61.9°$ (C=1, methanol).

(6) Into 5 ml of ethanol, were dissolved 0.5 g of racemic threo-N-phthaloyl-3-(3,4-dihydroxyphenyl)serine and 0.24 g of ephedrine. The resulting solution was left standing for 15 hours at 0° to 5° C. and the precipitated crystals were collected by filtration to yield 0.3 g of the ephedrine salt of D-threo-N-phthaloyl-3-(3,4-dihydroxyphenyl)serine; metling point, 139° C. (decomp.); $[\alpha]_D^{20} = -15.2°$ (C=1, methanol).

EXAMPLE 14

(1) A solution was prepared from 1.0 g of L-threo-N-phthaloyl-3-(3,4-methylenedioxyphenyl)serine obtained in Example 7, 1.5 ml of ethyl mercaptan, and 30 ml of dried dichloromethane. To the solution maintained at −10° to 0° C. with stirring, was added 2.25 g of anhydrous aluminum chloride. The mixture was stirred for 4 hours at −10° to 0° C. and added dropwise into 20 ml of a 5% aqueous oxalic acid solution at 20° C. or below. The mixture was stirred at 30° to 40° C. for 30 minutes and then at room temperature for another 30 minutes. The precipitated crystals were collected by filtration to yield 0.76 g of L-threo-N-phthaloyl-3-(3,4-dihydroxyphenyl)serine; melting point, 205°–208° C.; $[\alpha]_D^{20} = -91.0°$ (C=1, methanol).

(2) Into 5 ml of ethanol, was dissolved 0.52 g of L-threo-N-phthaloyl-3-(3,4-dihydroxyphenyl)serine obtained above in (1), followed by the addition of 0.11 g of hydrazine hydrate. The mixture was heated under reflux for 2 hours and the reaction mixture was concentrated under reduced pressure. The residue was mixed with 4 ml of methanol, then adjusted to pH 1 with concentrated hydrochloric acid, stirred for 30 minutes, and separated from the insolubles by filtration. The filtrate was adjusted to pH 5.6 with 30% aqueous sodium hydroxide solution and the precipitated crystals were collected by filtration to yield 0.36 g of L-threo-3-(3,4-dihydroxyphenyl)serine; melting point, 223°–226° C.; $[\alpha]_D^{20} = -37.4°$ (C=1, 1N hydrochloric acid).

EXAMPLE 15

(1) A solution was prepared from 3 g of L-threo-N-phthaloyl-3-(3,4-methylenedioxyphenyl)serine obtained in Example 8-(5), 4.5 ml of ethyl mercaptan, and 90 ml of dried dichloromethane. To the solution cooled at −10° to 0° C. with stirring, was added 6.75 g of anhydrous aluminum chloride. The mixture was stirred for 4 hours at −10° to 0° C. and added dropwise into 60 ml of a 5-% aqueous oxalic acid solution at 20° C. or below. The mixture was stirred at 30° to 40° C. for 30 minutes and then at room temperature for another 30 minutes. The precipitated crystals were collected by filtration to yield 2.24 g of L-threo-N-phthaloyl-3-(3,4-dihydroxyphenyl)serine; melting point, 200°–208° C.; $[\alpha]_D^{20} = -90.2°$ (C=1, methanol).

(2) Into 20 ml of ethanol, was dissolved 2.06 g L-threo-N-phthaloyl-3-(3,4-dihydroxyphenyl)serine obtained above in (1), followed by the addition of 0.45 g of hydrazine hydrate. The mixture was heated under reflux for 2 hours and the reaction mixture was concentrated under reduced pressure. The residue was mixed with 20 ml of methanol, then adjusted to pH 1 with concentrated hydrochloric acid, stirred for 30 minutes, and separated from the insolubles by filtration. The filtrate was adjusted to pH 5.6 with a 30% sodium hydroxide solution and the precipitated crystals were collected by filtration to yield 1.07 g of L-threo-3-(3,4-dihydroxyphenyl)serine; melting point, 223°–225° C.; $[\alpha]_D^{20} = -37.4°$ (C=1, 1N hydrochloric acid).

EXAMPLE 16

(1) A solution was prepared from 4.35 g of L-erythro-N-phthaloyl-3-(3,4-methylenedioxyphenyl)serine obtained in Example 9-(3), 7.5 g of n-octyl mercaptan, and 60 ml of dried dichloroethane. To the solution cooled at −10° to 0° C. with stirring, was added 6.85 g of anhydrous aluminum chloride. The mixture was stirred for 4 hours at −10° to 0° C. and added dropwise into 90 ml of a 5% aqueous oxalic acid solution at 20° C. or below. The mixture was stirred at 30° to 40° C. for 30 minutes and then at room temperature for another 30 minutes, and allowed to separate into aqueous and dichloroethane layers. The aqueous layer was extracted with ethyl acetate. The extract was washed with saturated aqueous sodium cloride solution, dried over anhydrous magnesium sulfate, and evaporated under reduced pressure to yield 2.27 g of L-erythro-N-phthaloyl-3-(3,4-dihydroxyphenyl)serine in oily form; $[\alpha]_D^{26} = -154.7°$ (C=1, methanol).

IR: νliquid paraffin (cm$^{-1}$): 3500, 1700, 1605, 1510, 1270, 1160, 1110, 1030, 930.

(2) Into 20 ml of ethanol, was dissolved 2.06 g of L-erythro-N-phthaloyl-3-(3,4-dihydroxyphenyl) serine obtained above in (1), followed by the addition of 0.45 g of hydrazine hydrate. The mixture was heated under reflux for 2 hours, then the reaction mixture was adjusted to pH 1.0 with concentrated hydrochloric acid at room temperature, stirred for 30 minutes, and separated from the insolubles by filtration. The filtrate was adjusted approximately to pH 5.5–5.6 and evaporated under reduced pressure. The residue was dissolved with heating in 4.4 g of water, left standing for 15 hours at 0° to 5° C., and the precipitated crystals were collected by filtration to yield 1.12 g of L-erythro-3-(3,4-dihydroxyphenyl)serine; $[\alpha]_D^{21} = +51.6°$ (C=1, 1N HCl); melting point, 190°–193° C. (decomp.).

| Elementary analysis: | C % | H % | N % |
| --- | --- | --- | --- |
| Calculated for C$_9$H$_{11}$O$_5$N.2 1/6H$_2$O | 43.04 | 6.11 | 5.54 |
| Found | 43.00 | 6.08 | 5.57 |

EXAMPLE 17

(1) A solution was prepared from 20 g of D-threo-N-phthaloyl-3-(3,4-methylenedioxyphenyl)serine, 41.2 g of n-octyl mercaptan, and 600 ml of dichloroethane. To the solution cooled at 0° to 5° C. with stirring, was added 37.6 g of anhydrous aluminum chloride. The mixture was stirred for 4 hours at 0° to 5° C. and added dropwise into 1,000 ml of a 5% aqueous acid solution at 5° C. or below. The mixture was stirred for 30 minutes at 30° to 40° C., and allowed to separate into aqueous and dichloroethane layers at room temperature. The aqueous layer was extracted 4 times with 300 ml of ethyl acetate. The extracts were washed three times with saturated aqueous sodium chloride solution, dried over anhydrous magnesium sulfate, and concentrated under reduced pressure. The residue was mixed with an ethyl acetate-toluene mixture and the precipitated crystals were collected by filtration to yield 13.1 g of D-threo-N-phthaloyl-3-(3,4-dihydroxyphenyl)serine; melting point; 204°–209° C.; $[\alpha]_D = +90.5°$ (C=1, methanol).

(2) Into 100 ml of ethanol, was dissolved 10.3 g of D-threo-3-(3,4-dihydroxyphenyl)serine obtained above in (1), followed by the addition of 2.25 g of hydrazine hydrate. The mixture was heated under reflux for 2 hours and the reaction mixture was concentrated under reduced pressure. The residue was mixed with 100 ml of methanol, adjusted to pH 1 with concentrated hydrochloric acid, then stirred for 30 minutes, and freed from the insolubles by filtration. The filtrate was adjusted to pH 5.6 with a 30% aqueous sodium hydroxide solution and the precipitated crystals were collected by filtration to yield 5.2 g of D-threo-3-(3,4-dihydroxyphenyl)serine; melting point, 224°–226° C.; $[\alpha]_D^{20} = +38.0°$ (C=1, 1N HCl).

EXAMPLE 18

(1) Using 4.35 g of D-erythro-N-phthaloyl-3-(3,4-methylenedioxyphenyl)serine obtained in Example 11, the reaction was carried out in a manner similar to that in Example 16-(1), to yield 2.30 g of D-erythro-N-phthaloyl-3-(3,4-dihydroxyphenyl)serine in oily form; $[\alpha]_D^{28} = +186.4°$ (C=1, DMSO).

IR: νliquid paraffin (cm$^{-1}$): 3500, 1700, 1605, 1510, 1270, 1160, 1110, 1030, 930.

(2) Using 2.06 g of D-erythro-N-phthaloyl-3-(3,4-dihydroxyphenyl)serine obtained above in (1), the reaction was carried out as in Example 16-(2) to obtain 1.10 g of D-erythro-3-(3,4-dihydroxyphenyl)serine; $[\alpha]_D^{22} = -48.2°$ (C=1, 1N HCl); melting point, 190°–193° C. (decomp.).

| Elementary analysis: | C % | H % | N % |
|---|---|---|---|
| Calculated for C9H11O5N.2H2O | 43.37 | 6.07 | 5.62 |
| Found | 43.10 | 6.08 | 5.48 |

What is claimed is:

1. A process for producing 3-(3,4-dihydroxyphenyl)serine, represented by the formula:

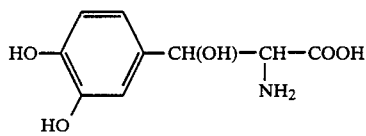
(I)

which comprises allowing the N-phthaloyl-3-(3,4-methylenedioxyphenyl)serine, represented by the formula:

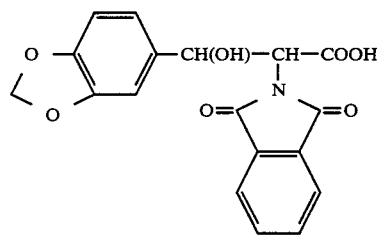
(VI)

to react with a Lewis acid selected from the group consisting of aluminum trichloride, aluminum tribromide, boron trichloride, and boron tribromide to form N-phthaloyl-3-(3,4-dihydroxyphenyl)-serine, represented by the formula:

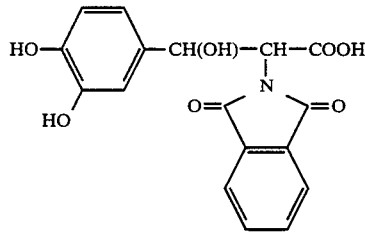
(II)

and removing the phthaloyl group with hydrazine hydrate therefrom.

2. A process according to claim 1, wherein the compounds represented by the formulas (I), (VI), and (II) are the optically active form.

3. A process for producing L-3-(3,4-dihydroxylphenyl)serine, represented by the formula:

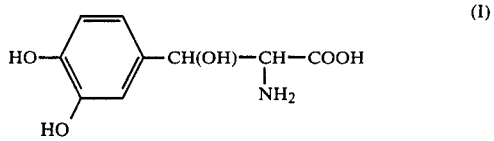
(I)

which comprises subjecting a racemic N-phthaloyl-3-(3,4-methylenedioxyphenyl)serine, represented by the formula:

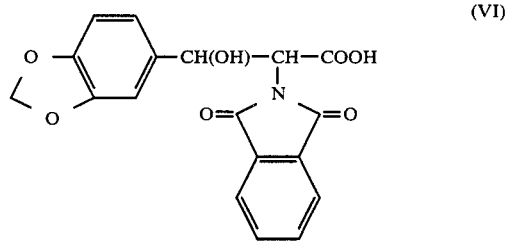
(VI)

to optical resolution through reaction with an optically active amine selected from the group consisting of strychinine, cinconidine, l-norephedrine, S-2-amino-1,1-diphenyl-1-propanol, and L-3-hydroxy-3(4-nitrophenyl)-2-amino-1-propanol to yield L-N-phthaloyl-3-(3,4-methylenedioxyphenyl)serine, allowing the resulting compound to react with a Lewis acid selected from the group consisting of aluminum trichloride, aluminum tribromide, boron trichloride, and boron tribromide to form L-N-phthaloyl-3-(3,4-dihydroxyphenyl)serine, represented by the formula:

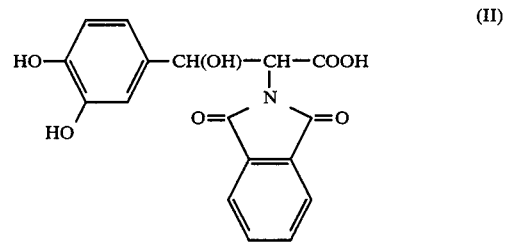
(II)

and removing the phthaloyl group with hydrazine hydrate therefrom.

4. A process for producing L-3-(3,4-dihydroxyphenyl)serine, represented by the formula:

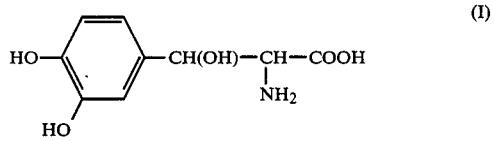
(I)

which comprises allowing a racemic 3-(3,4-methylenedioxyphenyl)-serine, represented by the formula:

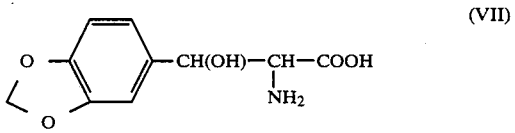
(VII)

to react with N-carbomethoxy- or N-carbomethoxyphthalimide to yield a racemic N-phthaloyl-3-(3,4-methylenedioxyphenyl)serine, represented by the formula:

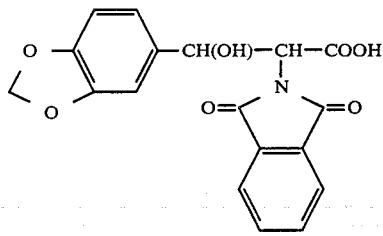
(VI)

subjecting the resulting compound to optical resolution through the reaction with an optically active amine selected from the group consisting of strychinine, cinconidine, l-norephedrine, S-2-amino-1,1-diphenyl-1-propanol, and L-3-hydroxy-3-(4-nitrophenyl)-2-amino-1-propanol to yield L-N-phthaloyl-3-(3,4-methylenedioxyphenyl)serine, allowing the resulting compound to react with a Lewis acid selected from the group consisting of aluminum trichloride, aluminum tribromide, boron trichloride, and boron tribromide, to form L-N-phthaloyl-3-(3,4-dihydroxyphenyl)serine, represented by the formula:

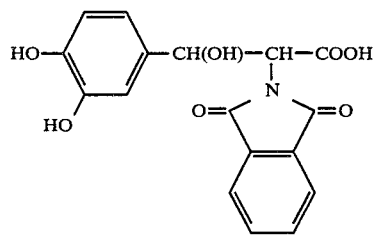
(II)

and removing the phthaloyl group with hydrazine hydrate therefrom.

5. A process for producing L-3-(3,4-dihydroxyphenyl)serine, represented by the formula:

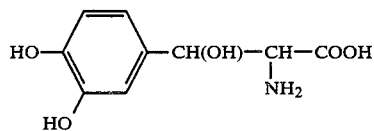
(I)

which comprises allowing a racemic 3-(3,4-methylenedioxyphenyl)-serine, represented by the formula:

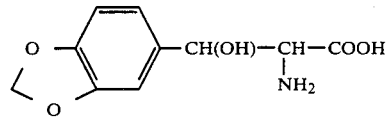
(VII)

to react with N-carbomethoxy- or N-carboethoxyphthalimide to yield a racemic N-phthaloyl-3-(3,4-methylenedioxyphenyl)serine, represented by the formula:

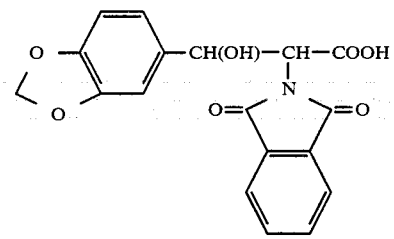
(VI)

subjecting the resulting compound to optical resolution through the reaction with l-norephedrine to yield L-N-phthaloyl-3-(3,4-methylenedioxyphenyl)serine, allowing the resulting compound to react with aluminum trichloride in the presence of one mole of n-octylmercaptan per one mole of aluminum trichloride to yield L-N-phthaloyl-3-(3,4-dihydroxyphenyl)serine, represented by the formula:

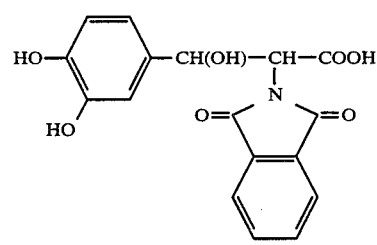
(II)

and removing the phthaloxy group with hydrazine hydrate therefrom.

6. A process according to claim 5, wherein the compounds represented by the formulas (I), (VII), (VI), and (II) are the threo form.

7. An N-phthaloylserine derivative represented by the general formula:

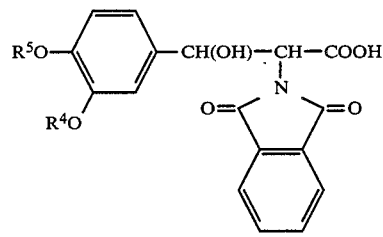

wherein $R^4$ and $R^5$ each represents a hydrogen atom or a methyl group, or $R^4$ and $R^5$; jointly form a methylene group.

* * * * *